(12) United States Patent
Hur

(10) Patent No.: US 7,109,039 B1
(45) Date of Patent: Sep. 19, 2006

(54) CHEMICAL COMPOSITION FOR DISSOLVING A SAMPLE TAKEN FROM SEMICONDUCTOR DEVICE FABRICATION EQUIPMENT AND METHOD FOR ANALYZING CONTAMINANTS ON THE EQUIPMENT USING THE CHEMICAL COMPOSITION

(75) Inventor: Yong-woo Hur, Kyungki-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 09/204,364

(22) Filed: Dec. 4, 1998

(30) Foreign Application Priority Data

Dec. 5, 1997 (KR) .................................. 97-66288

(51) Int. Cl.
 *G01N 21/17* (2006.01)
(52) U.S. Cl. ...................... 436/164; 436/175; 436/179
(58) Field of Classification Search ................ 436/14, 436/16, 83, 164, 171, 175, 179
See application file for complete search history.

(56) References Cited

U.S. PATENT DOCUMENTS

| | | | | |
|---|---|---|---|---|
| 3,520,656 A | * | 7/1970 | Yates et al. ................. | 423/345 |
| 5,026,135 A | * | 6/1991 | Booth ......................... | 385/130 |
| 5,294,763 A | * | 3/1994 | Chamberlain et al. ...... | 219/729 |
| 5,560,857 A | * | 10/1996 | Sakon et al. ................. | 510/175 |
| 5,686,314 A | * | 11/1997 | Miyazaki ..................... | 436/177 |
| 5,877,027 A | * | 3/1999 | Kemmochi et al. ......... | 436/175 |
| 6,290,777 B1 | * | 9/2001 | Imaoka et al. ............... | 134/1 |
| 6,896,744 B1 | * | 5/2005 | Morinaga et al. ............ | 134/28 |
| 2002/0101576 A1 | * | 8/2002 | Shabani et al. .............. | 356/36 |
| 2003/0000458 A1 | * | 1/2003 | Marumo et al. ............. | 117/200 |

OTHER PUBLICATIONS

Maxfield, B.W. et al. "Superconducting Penetration Depth of Niobium" Physical Review, vol. 139 (1965) pp. A 1515-A 1522.*
Kunze, J. et al. "Determination of titanium and zirconium wear debris in blood serum by means of HNO3/HF pressurized digestion using ICP—optical emission spectroscopy" Fresenius' Journal of Analytical Chemistry, vol. 361 (Jul. 1988) abstract only.*

* cited by examiner

*Primary Examiner*—Jeffrey R. Snay
(74) *Attorney, Agent, or Firm*—Volentine Francos & Whitt, PLLC

(57) ABSTRACT

A chemical for dissolving a sample taken from the semiconductor device fabrication equipment for analyzing the contaminants attached thereon, and a method of analyzing the contaminants thereby. The chemical composition is made of equal ports of sulfuric acid, hydrogen fluoride, and nitric acid. The method includes a) immersing a sample taken from semiconductor device fabrication equipment in the chemical composition; b) dissolving the sample in the chemical composition; c) cooling the dissolved sample; d) diluting the dissolved sample with deionized water and e) analyzing the diluted sample using either Atomic Absorption Spectrometer or by Atomic Emission Spectroscopy.

18 Claims, 2 Drawing Sheets

CHEMICAL COMPOSITION FOR DISSOLVING A SAMPLE TAKEN FROM SEMICONDUCTOR DEVICE FABRICATION EQUIPMENT AND METHOD FOR ANALYZING CONTAMINANTS ON THE EQUIPMENT USING THE CHEMICAL COMPOSITION

BACKGROUND OF THE INVENTION

1. Field of the Invention

The present invention relates to a chemical composition that dissolves a sample taken from semiconductor device fabrication equipment made of heat-resistant and acid-resistant materials including silicon carbide, quartz, and zirconium, and to a method of analyzing contaminants on the equipment sample after the sample is dissolved in the chemical composition.

2. Description of the Related Art

Quartz, which has high heat-resistance and acid-resistance, is normally used to make semiconductor device fabrication equipment, such as the tube in which the semiconductor device is fabricated using a high temperature processing gas, and the boat that is introduced into the tube for holding a plurality of wafers to be processed. However, the process conditions cause structural disorder in the crystal of the quartz so that the shape of the boat is distorted and the plurality of wafers housed therein are damaged.

To avoid the problems encountered by using quartz, semiconductor device fabrication equipment has recently been made of silicon carbide which has relatively better heat-resistance and acid-resistance than the quartz and a more stable structure.

Contaminants originating from the processing gas induced into the tube, or by-products of the reaction of the processing gases, adhere to the surface of semiconductor device fabrication equipment. These contaminants include boron, aluminum, and antimony, etc. Contaminants can cause shorts in the fabricated semiconductor device, or cause the device to malfunction due to variances in the operation voltage resulting from contamination on wafers that were prepared inside contaminated equipment.

Therefore, there is a great need for quantitative and qualitative methods to analyze the contaminants adhered to semiconductor device fabrication equipment. There are two ways to analyze such contamination: by non-destructive analysis and by destructive analysis.

The non-destructive method employs techniques such as GD-MS (Glow Discharge-Mass Spectrometer), GD-OED (Glow Discharge-Optical Emission Spectrometer), XRF (X-Ray Fluorescence), ICP-MS (Inductively Coupled Plasma-Mass Spectrometer), Laser, etc. Although the non-destructive methods permit analysis without obtaining a sample of the material, such as the boat or tube on which the contaminants have formed, they are not highly accurate.

Destructive methods which include Atomic Absorption Spectroscopy or Inductively Coupled Plasma-type Atomic Emission Spectroscopy, are more accurate but they require analysis of a sample of the semiconductor equipment on which the contaminants have adhered.

The Atomic Absorption Spectroscopy method operates on the theory that the amount of radiation absorbed by a sample that absorbs radiation having a specific wavelength, is proportional to the concentration of the atoms contained in the sample which is being analyzed. Therefore, after an object to be analyzed is dried inside a high temperature graphite reactor, ashed, and atomized, radiation having a specific wavelength which can be absorbed by targeted sample atoms, is irradiated onto the sample. The absorbance of radiation indicates the degree to which the targeted atoms inside the sample absorb the radiation, and provides a way to quantitatively and qualitatively analyze the kinds and the amount of the contaminants adhered to the sample.

Inductively Coupled Plasma-type Atomic Emission Spectroscopy requires generation of a plasma by supplying argon gas to the processing chamber and applying high-frequency voltage to the induction coil provided outside the processing chamber. Then, a reference solution is supplied to the stabilized plasma which causes the excited atom or ion of the targeted element in the solution to emit radiation. The radiation is analyzed through the spectroscope, and the kinds and the amount of the contaminants in the sample are quantitatively and qualitatively analyzed.

Analyzing contaminants using a destructive method is additionally complicated by the fact that the structure of the silicon carbide used to make the semiconductor device fabrication equipment is so stable. Silicon carbide is not dissolved by known chemical compositions and the silicon element of the silicon carbide also acts as matrix so that exact quantitative and qualitative analysis of the contaminants cannot be done.

SUMMARY OF THE INVENTION

The present invention is directed to a chemical composition for dissolving a sample taken from semiconductor device fabrication equipment made of silicon carbide, quartz, aluminum oxide or zirconium, and to a method of analyzing the contaminants adhered to the sample.

One object of the present invention is to provide a chemical composition and a method for analyzing the contaminants adhered on semiconductor device fabrication equipment made of silicon carbide, quartz, aluminum oxide, and zirconium compounds which compounds have good heat-resistance and good acid-resistance.

To achieve these and other advantages, the present invention provides a chemical composition for dissolving a sample taken from the semiconductor device fabrication equipment which composition is a mixture of equal amounts by volume of sulfuric acid, hydrogen fluoride, and nitric acid.

In another aspect, the present invention provides a method of analyzing contaminants adhering to a sample taken from semiconductor device fabrication equipment by: a) immersing the sample in a chemical composition comprising equal amounts by volume of sulfuric acid, hydrogen fluoride, and nitric acid; b) dissolving the sample in the chemical composition; c) cooling the dissolved sample to room temperature; d) diluting the dissolved sample with deionized water; and e) analyzing the diluted sample.

Any unwanted fumes remaining in the dissolved sample can be removed by irradiating infrared light onto the dissolved sample surface using an infrared lamp in order to increase the temperature of the dissolved sample thereby causing the fumes to evaporate. In a preferred embodiment, the temperature of the dissolved sample is increased to between about 60° C. and 80° C. by irradiating with an infrared lamp in order to remove unwanted fumes.

The immersing step of the analysis method can also include putting the chemical composition and the sample to a sample container, sealing the sample container, placing the sealed sample container in a pressure container for further sealing, placing the pressure container into a temperature-variable dry oven, and heating the chemical and the sample in the sample container.

In a preferred embodiment, heating the chemical composition and the sample further comprises increasing the inner temperature of the dry oven sequentially to a first lower inner temperature and then to a second higher inner temperature, which second higher inner temperature is then maintained for a period of time sufficient to permit the sample to dissolve. In a preferred embodiment, the first lower inner temperature is in a range of from about 100° C. to about 140° C., and the second higher inner temperature is in a range of from about 200° C. to about 260° C.

In another preferred embodiment, the inner temperature of the dry oven is increased to the second higher inner temperature by repeating the following steps continually and in the following sequence: a) increasing the inner temperature of the dry oven for about 140 to 160 seconds after the first lower inner temperature has been reached, until an intermediate temperature is reached, the intermediate temperature being above the first lower inner temperature and below the second higher inner temperature; (b) maintaining the first intermediate temperature reached in (a) for 3 to 6 seconds, (c) decreasing the inner temperature of the dry oven for 45 to 55 seconds; (d) increasing the inner temperature of the dry oven for about 140 to 160 seconds until another higher intermediate temperature is reached; (e) maintaining the higher intermediate temperature reached in (d) for 3 to 6 seconds, (f) decreasing the inner temperature of the dry oven for 45 to 55 seconds; (g) repeating (d), (e) and (f) until the second higher inner temperature is reached.

The sample can be silicon carbide, quartz, aluminum oxide or zirconium compounds. If the sample is silicon carbide, quartz or zirconium, the second higher inner temperature is maintained for about 22 to 26 hours. If the sample is aluminum oxide, the second higher temperature is maintained for 45 to 55 hours to dissolve the sample.

In another preferred embodiment, the dissolved sample is diluted by making a solution of about 10 to 20 weight percent of the dissolved sample and about 80 to 90 weight percent of deionized water, and it is analyzed by either Atomic Absorption Spectrometry or Atomic Emission Spectroscopy.

BRIEF DESCRIPTION OF THE DRAWINGS

The accompanying drawings illustrate embodiments of the invention, in which.

DETAILED DESCRIPTION OF THE PREFERRED EMBODIMENTS

Figure 3:
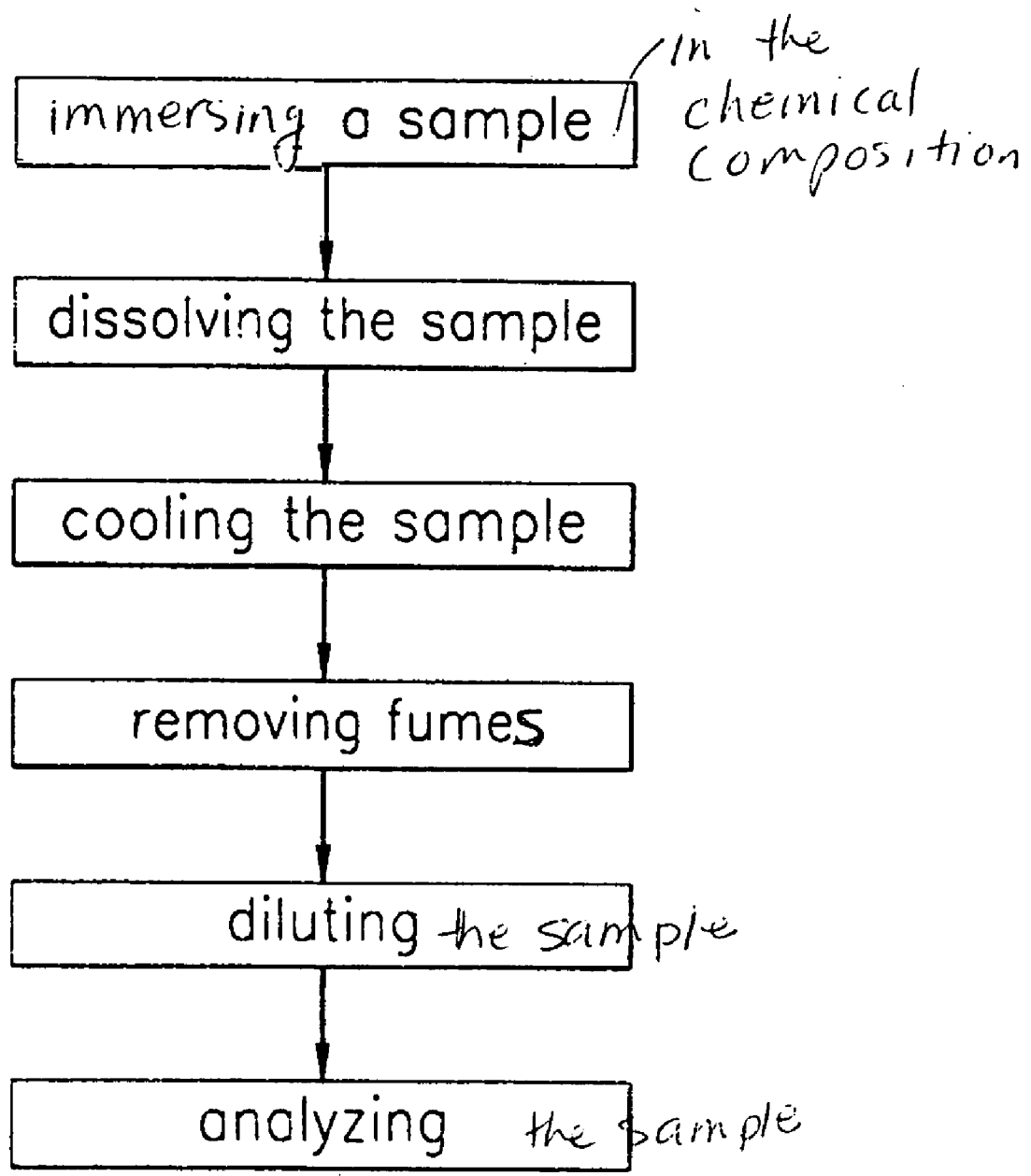
FIG. 3 is a processing sequence illustrating the method of analyzing contaminants using the chemical composition for dissolving the sample taken from the semiconductor device fabrication equipment according to the present invention.

A chemical composition for dissolving silicon carbide, quartz, aluminum oxide, or zirconium samples taken from semiconductor device fabrication equipment will now be described in detail along with a method for analyzing contaminants adhering to the sample, with reference to FIG. 1 though FIG. 3.

The chemical composition for dissolving the sample of the semiconductor device fabrication equipment according to the present invention is a mixture of equal volumes of sulfuric acid ($H_2SO_4$), hydrogen fluoride (HF), and nitric acid ($HNO_3$).

The method of analyzing the contaminants adhered to the sample of semiconductor device fabrication equipment will be described in detail.

Figure 2:
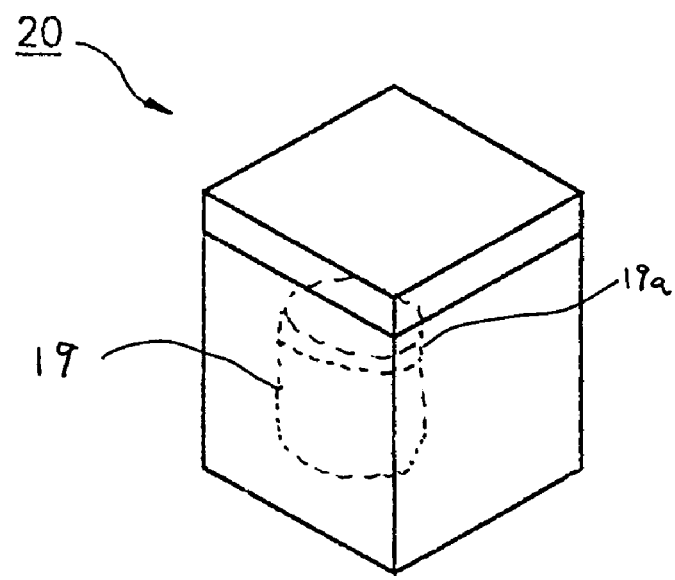
FIG. 2 illustrates a pressure container used in the method of analyzing the contaminants on the semiconductor device fabrication equipment according to the present invention.

First, a sample of material is taken from the semiconductor device fabrication equipment in order to analyze the contaminants adhered thereto. The sample is typically formed of silicon carbide, quartz, or zirconium compounds which have high heat and acid-resistance. Typically, 0.1 to 0.3 g of sample, preferably 0.2 g is taken. The sample is then introduced into a sample container 19 that can be sealed. In a preferred embodiment, 15 ml of the chemical composition is used to dissolve the sample, thus 5 ml of each of sulfuric acid, hydrogen fluoride, and nitric acid are mixed to form the chemical composition. After the chemical composition is added to the sample container 19, the lid 19a of the container is closed, and the container 19 is introduced into a pressure container 20 made of stainless steel and shown in FIG. 2. The configuration of the pressure container 20 can be varied, as long as it holds the sample container 19 and fits into the dry oven 10.

Figure 1:
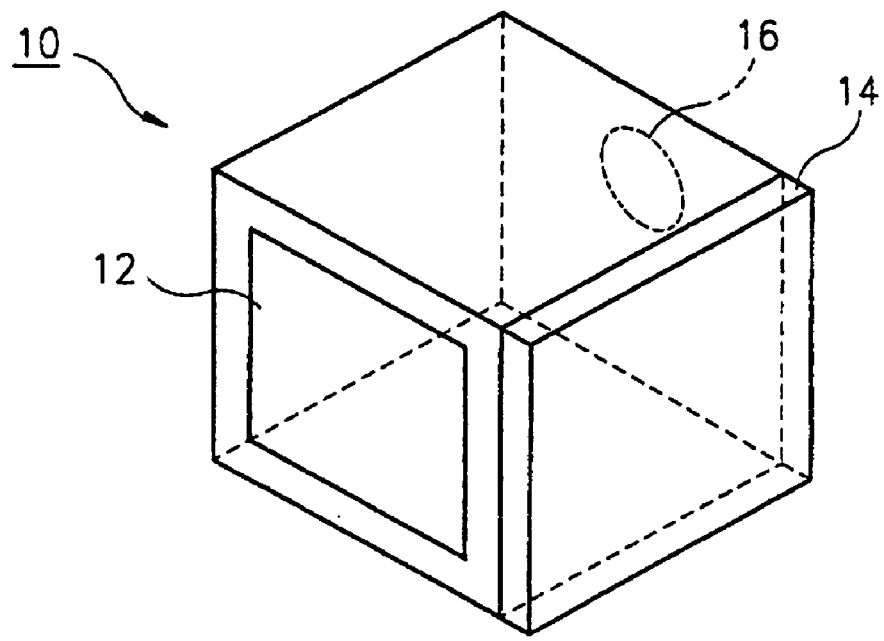
FIG. 1 is a schematic drawing of the dry oven used in the method of analyzing the contaminants on the semiconductor device fabrication equipment according to the present invention.

The pressure container 20 is then introduced into a dry oven 10 as is shown in FIG. 1. The dry oven 10 has a heater 14 controlled by controller (not shown) located in one side of the dry oven, and a stainless steel fan 16 provided on one side wall for inducing air flow with the outside of the dry oven 10, and a door 12. The temperature of the dry oven 10 is increased sequentially, to a first lower inner temperature and then to a second higher inner temperature. The second higher inner temperature is maintained for an extended period of time to permit the sample to dissolve. To raise the temperature in the dry oven 10, the heater 14 is driven by a controller for about 10 to 20 minutes, preferably for 15 minutes, in order to increase the inner temperature of the dry oven from room temperature to a first lower inner temperature of about 100° C. to 140° C., most preferably about 120° C. After the first lower inner temperature has been reached, the heater 14 is again turned on to increase the temperature of the dry oven 10 to the second higher inner temperature of about 200° C. to 260° C., preferably of about 230° C., which raises the temperature of the sample and the chemical composition in the container accordingly.

The second higher inner temperature is reached by increasing the inner temperature of the dry oven 10 incrementally by repeating a temperature cycle sequence of increasing, then maintaining, and decreasing the temperature in the dry oven 10 by selectively operating/adjusting the heater 14 and the fan 16. Increasing the inner dry oven temperature by increments to go from the first lower to the second higher inner temperature prevents damage to the dry oven 10 itself and to the pressure container 20 that would otherwise be caused by a rapid and continuous increase of the dry oven temperature.

The second higher inner temperature is achieved by implementing a temperature cycling sequence including: (a) increasing the inner temperature of the dry oven for about 140 to 160 seconds after the first lower inner temperature has been reached, until an intermediate temperature is reached, the intermediate temperature being above the first lower inner temperature and below the second higher inner temperature; (b) maintaining the first intermediate temperature reached in (a) for 3 to 6 seconds; (c) decreasing the inner temperature of the dry oven for 45 to 55 seconds; (d) increasing the inner temperature of the dry oven for about 140 to 160 seconds until another higher intermediate temperature is reached; (e) maintaining the intermediate temperature reached in (d) for 3 to 6 seconds; (f) decreasing the inner temperature of the dry oven for 4.5 to 55 seconds; (g) repeating (d), (e) and (f) until the second higher inner temperature is reached. The cycling sequence to achieve the second higher inner temperature of about 200° C. to 260° C. typically involves driving the heater 14 for about 10 to 20 minutes, preferably for about 15 minutes.

Once the inner temperature in the dry oven 10 reaches about 200° C. to 260° C. through the temperature cycling sequence set forth above, it is maintained within a narrow range in the dry oven 10 over an extended period of time ranging from about 22 to 55 hours depending on the sample being dissolved. The increase of the inner temperature in the dry oven 10 to the second higher inner temperature, causes the inner pressure of the sample container to rise to from about 1000 to 4000 PSI (Pounds Per Square Inch). The combination of the high temperature and high pressure inside the sample container causes the sample of the semiconductor fabrication equipment to dissolve in the chemical composition of the present invention which has equal parts sulfuric acid, hydrogen fluoride, and nitric acid. For example, where the sample to be dissolved is made of silicon carbide, quartz or zirconium, the inner temperature of the dry oven 10 is maintained at the second higher inner temperature of about 200° C. to 260° C. for about 22 to 26 hours, preferably for 24 hours.

After the sample has dissolved, the inner temperature in the dry oven 10 is decreased for 20 to 40 minutes, preferably for about 30 minutes, by turning the heater 14 off. After the heater has been turned off for about 30 minutes, the pressure container 20 can be removed from the dry oven 10. The inner temperature of the pressure container 20 is then allowed to decrease further to room temperature.

Once the pressure container reaches room temperature, the sample container 19 is taken out of the pressure container 20 and its lid 19a is opened to permit any elements evaporated from the dissolved sample to escape. In the instance where silicon is contained in the dissolved sample, infrared radiation is then irradiated onto the surface of the dissolved sample using an infrared radiation lamp to raise the temperature of the sample to about 60° C. to 80° C., preferably to about 70° C., in order to evaporate and hence remove any unwanted silicon fluoride gas ($SiF_4$). Silicon must be removed in order to analyze the sample because it otherwise acts a matrix obstructing the quantitative analysis of the sample thereby decreasing the accuracy of the analysis. The silicon in the dissolved sample reacts with the hydrogen fluoride in the chemical composition to form silicon fluoride ($SiF_4$) gas which is volatile and can be easily evaporated at temperatures of from about 60° C. to 80° C.

After the fumes have been removed, the sample is diluted with deionized water. In a preferred embodiment, 10 to 20% of the sample by weight, and 80 to 90% deionized water by weight are mixed together for the dilution. In a most preferred embodiment, 15% of the sample by weight, and 85% deionized water by weight are mixed together. Finally, the diluted sample is analyzed using either Atomic Absorption Spectrometry or Atomic Emission Spectroscopy.

Where the sample is aluminum oxide ($Al_2O_3$), the same processing steps outlined above are performed, except that a second higher inner temperature of about 230° C. in the dry oven 10 is maintained for about 45 to 55 hours, preferably for 50 hours, before cooling and removing any unwanted fumes contained in the dissolved sample by irradiating infrared light onto the surface of the dissolved sample.

Where the sample is formed of zirconium, the same processing steps outlined above are performed, including irradiating infrared light onto the surface of the dissolved sample to remove unwanted fumes. A standard silicon carbide sample JCRM0222 (Japan Ceramic Reference Material 022) for which the identity of the contaminants and the exact amount of contaminant adhered to the standard sample were already known was analyzed using the present methods and chemical composition to test their accuracy and reliability. Table 1 illustrates the results obtained by analyzing the contaminants adhered to the standard sample JCRM0222 using the method of the present invention and compares these values to the reference values of the standard sample for the elements listed in the table.

TABLE 1

Analysis of Impurities Adhered to the Equipment Sample (Unit, %)

| IMPURITIES | REFERENCE VALUE OF STANDARD SAMPLE | ANALYZED VALUE OF STANDARD SAMPLE |
|---|---|---|
| Al | 0.58 | 0.060 |
| Fe | 0.51 | 0.053 |
| Ca | 0.025 | 0.027 |
| Mg | 0.005 | 0.005 |
| Cr | 0.006 | 0.007 |
| Ti | 0.003 | 0.003 |
| V | Below 0.001 | Below 0.001 |
| Ni | 0.001 | 0.001 |
| Mn | 0.001 | 0.001 |
| Zr | 0.001 | 0.001 |

Referring to Table 1, which compares the known reference amount of each impurity adhered to the standard sample with the amount of impurity measured experimentally using the analysis method of the present invention, it can be seen that the analysis results for Al, Fe, and Ca show a small but consistent increase of 0.002 above the known reference values. The analysis results for Mg, Cr, Ti, V, Ni, Mn, and Zr obtained using the analysis method of the present invention show no differences at all from the known reference values for these impurities. The results set forth in Table 1 show that the results obtained using the method of analyzing the contaminants of the present invention are highly reliable.

Table 2 shows the results of analyzing impurities adhered to various samples taken from several different locations in the semiconductor device fabrication equipment by employing the analysis method of present invention. The samples were taken from an wasted boat made of silicon carbide. The results in Table 2 are the average of the values obtained using atomic absorption and atomic emission spectroscopy.

TABLE 2

Analysis of Impurities Adhered to the Equipment Sample (Unit, ppm)

|  | Al | Fe | Ca | Mg | Cr | Ti | V | Ni | Mn | Zr |
|---|---|---|---|---|---|---|---|---|---|---|
| Sample 1 | 619 | 163 | 143 | 34.7 | — | 86.5 | 103 | 34.6 | 2.76 | 15.2 |
| Sample 2 | 604 | 163 | 144 | 34.8 | — | 35.3 | 100 | 33.6 | 2.86 | 15.5 |

TABLE 2-continued

Analysis of Impurities Adhered to the Equipment Sample (Unit, ppm)

|  | Al | Fe | Ca | Mg | Cr | Ti | V | Ni | Mn | Zr |
|---|---|---|---|---|---|---|---|---|---|---|
| Sample 3 | 610 | 161 | 150 | 34.7 | — | 84.5 | 97.7 | 35.5 | 2.74 | 15.36 |
| Sample 4 | 608 | 167 | 152 | 34.6 | 8.55 | 86.7 | 114 | 37.3 | 2.88 | 16.1 |
| Sample 5 | 616 | 170 | 150 | 35.4 | 7.91 | 87.3 | 114 | 35.7 | 2.83 | 16.8 |
| Sample 6 | 624 | 164 | 148 | 35.0 | 13.5 | 85.3 | 115 | 36.7 | 2.97 | 15.9 |
| Sample 7 | 614 | 164 | 146 | 34.6 | 9.99 | 84.6 | 119 | 38.7 | 2.68 | 16.0 |
| Sample 8 | 614 | 165 | 148 | 34.8 | 9.99 | 85.7 | 109 | 36.0 | 2.82 | 15.8 |
| Standard Deviation (RSD) (%) | 1.1 | 1.8 | 2.3 | 0.8 | 2.5 | 1.3 | 7.8 | 4.7 | 3.5 | 3.5 |

The results set forth in Table 2 show the following standard deviations: Al 1.1%, Fe 1.8%, Ca 2.3%, Mg 0.8%, Cr 2.5%, Ti 1.3%, V 7.8%, Ni 4.7%, Mn 3.5%, and Zr 3.5%.

Accordingly, analyzing the contaminants adhered to samples taken from semiconductor device fabrication equipment using to the present invention shows a standard deviation in the range of from about 0.8 to 7.8%.

The experimental results show that the methods of the present invention are effective to analyze the samples qualitatively (i.e., to determine which elements are present in the contaminant) and the quantitatively (i.e., to determine how much contamination is contributed by each element). Samples to be analyzed using the methods of the present invention may be taken from the tube or the boat; the samples may be made of quartz, silicon carbide, aluminum oxide, or zirconium compounds; and the contaminants may be analyzed using either Atomic Absorption Spectroscopy or Atomic Emission Spectroscopy.

The present invention is not limited to the embodiment, set forth above, and it is clearly understood that many variations may be made within the scope of the present invention by anyone skilled in the art.

What is claimed is:

1. A method of analyzing contaminants adhering to a sample taken from semiconductor device fabrication equipment comprising:
    a) immersing the sample in a chemical composition solution comprising equal amounts by volume of sulfuric acid, hydrogen fluoride, and nitric acid;
    b) dissolving the sample in the chemical composition solution by heating the chemical composition solution to a first lower inner temperature and then to a second higher inner temperature, and maintaining the second higher inner temperature for a predetermined period of time;
    c) cooling the chemical composition solution containing the dissolved sample to room temperature;
    d) diluting the cooled chemical composition solution containing the dissolved sample with deionized water; and
    e) analyzing the diluted chemical composition solution containing the dissolved sample.

2. The method of claim 1, further comprising after said cooling, removing any fumes contained in the chemical composition solution containing the dissolved sample.

3. The method of claim 2, wherein said removing further comprises irradiating infrared light onto the chemical composition solution containing the dissolved sample surface using an infrared lamp in order to increase the temperature of the dissolved sample thereby causing any fumes in the dissolved sample to evaporate.

4. The method of claim 3, wherein during said removing, the temperature of the chemical composition solution containing the dissolved sample is increased to between about 60° C. and 80° C. by irradiating the sample with the infrared lamp.

5. The method of claim 1, wherein the immersing further comprises,
    (a) adding the chemical composition solution and the sample to a sample container,
    (b) sealing the sample container,
    (c) placing the sealed sample container in a pressure container for further sealing,
    (d) placing the pressure container into a temperature-variable dry oven, and
    (e) raising the temperature in the dry oven to thereby heat the chemical composition solution and the sample in the sample container.

6. The method of claim 5, wherein the first lower inner temperature is in a range of from about 100° C. to about 140° C.

7. The method of claim 5, wherein the second higher inner temperature is in a range of from about 200° C. to about 260° C.

8. The method of claim 5, wherein said increasing of the inner temperature of the dry oven to the second higher inner temperature is performed with a temperature cycling sequence comprising,
    (a) increasing the inner temperature of the dry oven for about 140 to 160 seconds after the first lower inner temperature has been reached, until an intermediate temperature is reached, the intermediate temperature being above the first lower inner temperature and below the second higher inner temperature;
    (b) maintaining the first intermediate temperature reached in (a) for 3 to 6 seconds;
    (c) decreasing the inner temperature of the dry oven for 45 to 55 seconds;
    (d) increasing the inner temperature of the dry oven for about 140 to 160 seconds until another higher intermediate temperature is reached;
    (e) maintaining the higher intermediate temperature reached in (d) for 3 to 6 seconds;
    (f) decreasing the inner temperature of the dry oven for 45 to 55 seconds;
    (g) repeating (d), (e) and (f) until the second higher temperature is reached.

9. The method of claim 1, wherein the sample contains one of silicon carbide, quartz or zirconium.

10. The method of claim 8, wherein the second higher inner temperature is maintained for about 22 to 26 hours to dissolve the sample.

11. The method of claim 5, wherein the cooling of the dissolved sample further comprises, decreasing the inner temperature of the dry oven, and removing the pressure container from the dry oven.

12. The method of claim 11, wherein decreasing the inner temperature of the dry oven is carried out for 20 to 40 minutes.

13. The method of claim 1, wherein said diluting is achieved by making a solution of about 10 to 20 weight percent of the chemical composition solution containing the dissolved sample and about 80 to 90 weight percent of deionized water.

14. The method of claim 1, wherein the analyzing is accomplished using an Atomic Absorption Spectrometer.

15. The method of claim 1, wherein the analyzing is accomplished using an Atomic Emission Spectroscope.

16. The method of claim 1, wherein during said immersing, about 0.1 to 0.3 g of the sample is immersed in about 10 to 20 ml of the chemical composition solution.

17. The method of claim 5, wherein the sample is aluminum oxide.

18. The method of claim 17, wherein the second higher inner temperature is maintained for about 45 to 55 hours to dissolve the sample.

* * * * *